United States Patent
Börner et al.

(10) Patent No.: US 7,612,240 B2
(45) Date of Patent: Nov. 3, 2009

(54) HALOPHOSPHOLANES AND THEIR PREPARATION

(75) Inventors: Armin Börner, Rostock (DE); Jens Holz, Kessin (DE); Juan Almena, Hanau (DE); Renat Kadyrov, Frankfurt (DE); Axel Monsees, Frankfurt (DE); Thomas Riermeier, Ober-Ramstadt (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/091,410

(22) PCT Filed: Oct. 4, 2006

(86) PCT No.: PCT/EP2006/067050
§ 371 (c)(1),
(2), (4) Date: Apr. 24, 2008

(87) PCT Pub. No.: WO2007/051679
PCT Pub. Date: May 10, 2007

(65) Prior Publication Data
US 2008/0287713 A1    Nov. 20, 2008

(30) Foreign Application Priority Data
Nov. 4, 2005    (DE) .................. 10 2005 053 079

(51) Int. Cl.
*C07F 9/02*    (2006.01)
(52) U.S. Cl. ........................................ 568/12
(58) Field of Classification Search .......... 568/12
See application file for complete search history.

(56) References Cited

U.S. PATENT DOCUMENTS 4,752,648 A * 6/1988 Weferling et al. ............. 558/10

FOREIGN PATENT DOCUMENTS

| WO | WO 03084971 | * 10/2003 |
| WO | 2005-049629 A1 | 6/2005 |
| WO | WO 2005049629 | * 6/2005 |

OTHER PUBLICATIONS

Krespan C. G., Langkammerer C. M.: "Fluorinated Heterocylic Derivatives of Sulfur, Selenium, and Phosphorus", Journal of Organic Chemistry, 1962, pp. 3584-3587, XP002419153 p. 3586.

* cited by examiner

*Primary Examiner*—Daniel M Sullivan
*Assistant Examiner*—Chukwuma O Nwaonicha
(74) *Attorney, Agent, or Firm*—Smith, Gambrell & Russell, LLP

(57) ABSTRACT

The present invention is directed to a process for preparing compounds of the general formula (I). Compounds of the general formula (I) are advantageous precursors for preparing phospholane catalysts, especially bisphospholane catalysts. The invention therefore likewise provides for the use of the substances in question for preparing these catalysts.

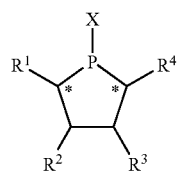

(I)

7 Claims, No Drawings

HALOPHOSPHOLANES AND THEIR PREPARATION

INTRODUCTION AND BACKGROUND

The present invention is directed to a process for preparing compounds of the general formula (I).

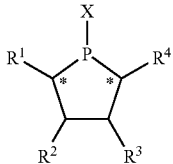
(I)

Compounds of the general formula (I) are advantageous precursors for preparing phospholane catalysts, especially bisphospholane catalysts. The invention therefore likewise provides such compounds, and also for the use of the substances in question for preparing these catalysts.

Enantiomerically enriched chiral ligands are used in asymmetric synthesis and asymmetric catalysis. An essential factor here is that the electronic properties and the stereochemical properties of the ligand are adjusted optimally to the particular catalysis problem. An important aspect of the success of these classes of compound is attributed to the creation of a particularly asymmetric environment of the metal centre by these ligand systems. In order to utilize such an environment for effective transfer of chirality, it is advantageous to control the flexibility of the ligand system as an inherent limitation of the asymmetric induction.

Within the substance class of the phosphorus-containing ligands, cyclic phosphines, especially the phospholanes, have achieved particular significance. Bidentate chiral phospholanes are, for example, the DuPhos and BPE ligands used in asymmetric catalysis. In the ideal case, however, a variously modifiable chiral ligand template is available, which can be varied within a wide range in relation to its steric and electronic properties.

The preparation of, for example, bidentate chiral phospholanes is effected generally by reacting the finished phospholane units with the catalyst backbone (WO2005/049629; EP1490379; DE102005014055). A successful method in this context works with phospholanes trialkylsilyl-substituted on the phosphorus atom, which are reacted with correspondingly halogen-substituted backbone compounds, for instance by the following scheme:

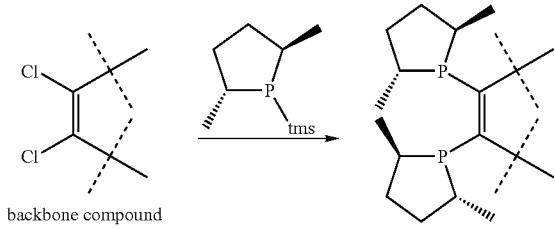

A further route is the reaction of aromatic-$(PH_2)_2$ compounds which are reacted under base catalysis with compounds of the following type (EP0592552, U.S. Pat. No. 5,329,015).

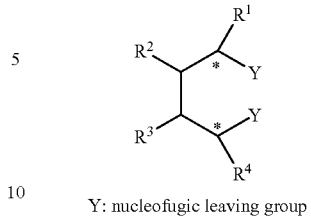

Y: nucleofugic leaving group

In the preparation routes described, the starting compounds are accordingly backbone compounds (see above) which possess very good nucleofugic leaving groups, or oxidation-sensitive phosphine-substituted aromatic systems are used.

SUMMARY OF THE INVENTION

It is an object of the present invention to specify a further process for preparing phospholane catalysts, wherein the catalysts to be prepared shall be obtained in a particularly simple and mild manner. Against the background of the prior art, the process according to the invention should appear to be advantageous viewed from the economic and also ecological standpoint.

These and further objects which are not specified in detail but are obvious from the prior art are solved by a process having the features of the subject Claim 1. Preferred embodiments of the present process are described in the subclaims dependent upon Claim 1. Claim 5 is directed to novel phospholanes which are used in the inventive use according to Claim 6.

By reacting, in a process for preparing compounds of the general formula (I)

(I)

in which

* is a stereogenic centre,

X=Cl, Br, I, especially preferably Cl, $R^1$, $R^4$ are each independently ($C_1$-$C_8$)-alkyl, ($C_1$-$C_8$)-alkoxy, HO—($C_1$-$C_8$)-alkyl, ($C_2$-$C_8$)-alkoxyalkyl, ($C_6$-$C_{18}$)-aryl, ($C_7$-$C_{19}$)-aralkyl, ($C_3$-$C_{18}$)-heteroaryl, ($C_4$-$C_{19}$)-heteroaralkyl, ($C_1$-$C_8$)-alkyl-($C_6$-$C_{18}$)-aryl, ($C_1$-$C_8$)-alkyl-($C_3$-$C_{18}$)-heteroaryl, ($C_3$-$C_8$)-cycloalkyl, ($C_1$-$C_8$)-alkyl-($C_3$-$C_8$)-cycloalkyl, ($C_3$-$C_8$)-cyclo-alkyl-($C_1$-$C_8$)-alkyl, $R^2$, $R^3$ are each independently $R^1$, OH or H, or $R^1$ and $R^2$ and/or $R^2$ and $R^3$ and/or $R^3$ and $R^4$, or $R^1$ and $R^3$ and/or $R^1$ and $R^4$, form a ($C_3$-$C_5$)-alkylene bridge together, compounds of the general formula (II)

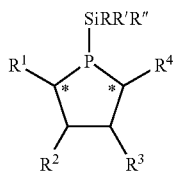

(II)

in which

*, $R^1$, $R^2$, $R^3$, $R^4$ are each as defined above, and R, R', R" may each independently be $R^1$, with halogenated compounds selected from the group consisting of double bond-free halocarbon compounds, especially chlorocarbon compounds, in which the ratio of carbon atoms to halogen atoms is $1:\geqq 2.5$, $CCl_3CN$, $CCl_3COOEt$, $CCl_{(3-x)}H_xC(=O)Cl$, $C_2Cl_4Br_2$, $Cl_2$, $Br_2$, $I_2$, intermediates (I) on the route to the preparation of phospholane catalysts, which permit the synthesis to start, for example, from metallated aromatics, are obtained in a surprisingly simple yet advantageous manner. These aromatics can be obtained in a simple manner by deprotonation, metal-halogen exchange or by ortho-metallation (Organometallics in Synthesis. A Manual, $2^{nd}$ Edition, Wiley 2002, Chapter 1, Editor Manfred Schlosser). The subject process thus provides the possibility of preparing the phospholane catalysts in question in a manner with effectively reversed polarity compared to the prior art. It is thus possible in a simple manner to prepare novel phospholane ligand structures which are not obtainable by reaction conditions detailed at the outset.

In a preferred manner, halogenated, especially chlorinated compounds from the group consisting of $CCl_4$, $CHCl_3$, $C_2Cl_6$, $C_2HCl_5$, $C_2Cl_4Br_2$, $Cl_2$, $Br_2$, $I_2$ are utilized in the process according to the invention. These are very particularly suitable for the reaction in question. Exceptionally preferred in this context is the use of $C_2Cl_6$.

The envisaged reaction may be carried out in any organic solvent considered useful by the person skilled in the art for the present purpose. This solvent should, however, prove to be inert with respect to the inventive reaction and additionally allow the inventive reaction to proceed in an essentially optimal manner. Particular preference is given in this context to a solvent which can be incorporated directly into an overall process for preparing the catalysts which comprises the inventive synthesis step. In this context, advantageous solvents are selected from the group consisting of halogenated solvents such as $CHCl_3$ or $CH_2Cl_2$. The person skilled in the art will select a solvent which is halogenated itself only to a very slight extent, if at all, under the reaction conditions. If appropriate, the use of a solvent can be dispensed with, or the solvent is simultaneously the halogenating agent.

The inventive reaction can proceed within a temperature range which can be determined by the person skilled in the art. It should be ensured that the reaction proceeds at a temperature at which a maximum conversion is ensured, but, on the other hand, the formation of by-products is largely suppressed. Advantageously, the reaction is carried out at a temperature of 0-120° C., preferably 20-80° C. and most preferably 30-50° C.

The present invention likewise provides compounds of the general formula (I)

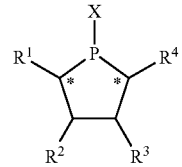

(I)

in which

* is a stereogenic centre,

X=Cl, Br, I, especially preferably Cl, $R^1$, $R^4$ are each independently $(C_1-C_8)$-alkyl, $(C_1-C_8)$-alkoxy, HO—$(C_1-C_8)$-alkyl, $(C_2-C_8)$-alkoxyalkyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_1-C_8)$-alkyl-$(C_3-C_8)$-cycloalkyl, $(C_3-C_8)$-cyclo-alkyl-$(C_1-C_8)$-alkyl, $R^2$, $R^3$ are each independently $R^1$, OH or H, or $R^1$ and $R^2$ and/or $R^2$ and $R^3$ and/or $R^3$ and $R^4$, or $R^1$ and $R^3$ and/or $R^1$ and $R^4$, form a $(C_3-C_5)$-alkylene bridge together.

The present invention likewise provides for the use of these compounds of the general formula (I) for preparing phospholane catalysts, especially bisphospholane catalysts. Advantageously, these catalysts contain a substructure of the following type:

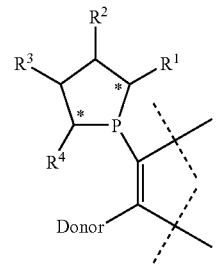

(Donor=atom having the means of forming a dative bond, e.g. $NR_2$, OR, SR, $PR_2$, etc.).

Very particular preference is given to the use of the compounds of the general formula (I) for preparing bisphospholane ligands, especially bisphospholanes, for example of the following structure:

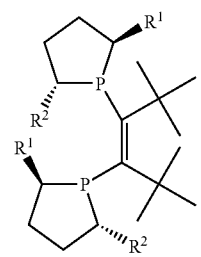

DETAILED DESCRIPTION OF INVENTION

To prepare the inventive compounds, for example of the general formula (I) where Hal=Cl, the procedure is analogous to the process described by Appel et al. (Chem. Ber. 1977, 110, 376-378). To this end, the appropriate phospholane silyl-substituted on the phosphorus atom (WO 2003084971, WO 2005049629) is admixed with the halogenating agent, preferably $C_2Cl_6$, in an inert organic solvent and heated gently. On completion of the reaction, the solvent can be distilled off under reduced pressure and the remaining residue can be distilled for the purpose of purification. Subsequently, the halophospholane, for example of the general formula (I) where Hal=Cl, can be reacted with a metallated aromatic in an organic solvent which is inert in turn. The workup is guided by the type of compound prepared and comprises methods familiar to the person skilled in the art, such as extraction, distillation or crystallization.

The person skilled in the art can prepare and react bromophospholanes in an analogous manner. To this end, Br2 or BrCl2CCCl2Br is used as the brominating agent. Iodophospholanes can be obtained analogously by the use of I2, isolated under some circumstances and reacted further.

The present process allows bisphospholane catalysts to be prepared starting from, for example, metallated aromatics in a particularly simple manner and with high yields. Metallated aromatics can be prepared easily by classical methods of organometallic chemistry (Organometallics in Synthesis. A Manual, $2^{nd}$ Edition, Wiley 2002, Chapter 1, Editor Manfred Schlosser). Successive metallation and reaction with halophospholanes of the general formula (I) or other halo-phosphine derivatives thus conveniently also allows bidentate, unsymmetrically substituted phosphinephospholane catalysts to be prepared (DE102005014055). Moreover, use of monometallated compounds allows ligands having only one phospholane and other donor atoms (such as N, S, O) to be prepared for the first time in a very simple manner.

$(C_1-C_8)$-Alkyl radicals are considered to be methyl, ethyl, n-propyl, isopropyl, n-butyl, isobutyl, sec-butyl, tert-butyl, pentyl, hexyl, heptyl or octyl including all of their bonding isomers. The $(C_1-C_8)$-alkoxy radical corresponds to the $(C_1-C_8)$-alkyl radical with the proviso that it is bonded to the molecule via an oxygen atom. $(C_2-C_8)$-Alkoxyalkyl means radicals in which the alkyl chain is interrupted by at least one oxygen function, where two oxygen atoms may not be joined to one another. The number of carbon atoms specifies the total number of carbon atoms present in the radical. A $(C_3-C_5)$-alkylene bridge is a carbon chain having three to five carbon atoms, this chain being bonded to the molecule in question via two different carbon atoms. The radicals described in the preceding paragraphs may be mono- or polysubstituted by halogens and/or nitrogen-, oxygen-, phosphorus-, sulphur-, silicon-containing radicals. These are in particular alkyl radicals of the type mentioned above which have one or more of these heteroatoms in their chain or which are bonded to the molecule via one of these heteroatoms.

$(C_3-C_8)$-Cycloalkyl is understood to mean cyclopropyl, cyclobutyl, cyclopentyl, cyclohexyl or cycloheptyl radicals, etc. They may be substituted by one or more halogens and/or nitrogen-, oxygen-, phosphorus-, sulphur-, silicon-containing radicals and/or have nitrogen, oxygen, phosphorus, sulphur atoms in the ring, for example 1-, 2-, 3-, 4-piperidyl, 1-, 2-, 3-pyrrolidinyl, 2-, 3-tetrahydrofuryl, 2-, 3-, 4-morpholinyl.

A $(C_3-C_8)$-cycloalkyl-$(C_1-C_8)$-alkyl radical denotes a cycloalkyl radical as detailed above which is bonded to the molecule via an alkyl radical as specified above.

In the context of the invention, $(C_1-C_8)$-acyloxy means an alkyl radical as defined above which has max. 8 carbon atoms and is bonded to the molecule via a COO function.

In the context of the invention, $(C_1-C_8)$-acyl means an alkyl radical as defined above which has max. 8 carbon atoms and is bonded to the molecule via a CO function.

A $(C_6-C_{18})$-aryl radical is understood to mean an aromatic radical having 6 to 18 carbon atoms. In particular, this includes compounds such as phenyl, naphthyl, anthryl, phenanthryl, biphenyl radicals, or systems of the above-described type fused to the molecule in question, for example indenyl systems which may optionally be substituted by halogen, $(C_1-C_8)$-alkyl, $(C_1-C_8)$-alkoxy, $NH_2$, $NH(C_1-C_8)$-alkyl, $N((C_1-C_8)$-alkyl$)_2$, OH, $CF_3$, $NH(C_1-C_8)$-acyl, $N((C_1-C_8)$-acyl$)_2$, $(C_1-C_8)$-acyl, $(C_1-C_8)$-acyloxy.

A $(C_7-C_{19})$-aralkyl radical is a $(C_6-C_{18})$-aryl radical bonded to the molecule via a $(C_1-C_8)$-alkyl radical.

In the context of the invention, a $(C_3-C_{18})$-heteroaryl radical denotes a five-, six- or seven-membered aromatic ring system composed of 3 to 18 carbon atoms and having heteroatoms, for example nitrogen, oxygen or sulphur, in the ring. Such heteroaromatics are considered in particular to be radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. This radical may be substituted with the same radicals as the abovementioned aryl radical.

A $(C_4-C_{19})$-heteroaralkyl is understood to mean a heteroaromatic system corresponding to the $(C_7-C_{19})$-aralkyl radical.

Useful halogens (Hal) include fluorine, chlorine, bromine and iodine.

PEG means polyethylene glycol.

N-acyl groups are understood to mean protecting groups which are generally used customarily in amino acid chemistry for the protection of nitrogen atoms. Particular examples include: formyl, acetyl, Moc, Eoc, phthalyl, Boc, Alloc, Z, Fmoc, etc.

A nucleofugic leaving group is understood essentially to mean a halogen atom, especially chlorine or bromine, or so-called pseudohalides. Further leaving groups may be tosyl, triflate, nosylate, mesylate.

In the context of the invention, the term enantiomerically enriched or enantiomeric excess is understood to mean the proportion of one enantiomer in a mixture with its optical antipode in a range of >50% and <100%. The ee value is calculated as follows:

$$([enantiomer1]-[enantiomer2])/([enantiomer1]+[enantiomer2])=ee \text{ value}$$

In the context of the invention, the specification of the inventive complexes and ligands includes all possible diastereomers, and shall also include the two optical antipodes of a particular diastereomer.

The literature references cited in this document are considered to be included in the disclosure.

A nucleofugic leaving group is understood essentially to mean a halogen atom, especially chlorine or bromine, or so-called pseudohalides. Further leaving groups may be tosyl, triflate, nosylate, mesylate.

EXAMPLES

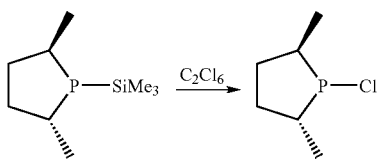

A three-necked flask equipped with a reflux condenser is initially charged with a solution of 12.57 g (53 mmol) of hexachlorohexane in 80 ml of abs. dichloromethane. With stirring, a solution of one equivalent (10.0 g) of trimethylsilylphospholane in 60 ml of dichloromethane is added dropwise. During this operation, the reaction mixture heats up to boiling. The reaction mixture is heated to boiling for a further half an hour and the solvent and the tetrachloroethylene formed are removed by distillation under gentle vacuum (400 mbar). The remaining residue was then distilled to obtain 5.7 g of a colourless liquid (b.p. $_{100}$=85-95° C., 71%).

NMR: $^1$H NMR (THF-$d_8$): 1.20 (3H, d, $CH_3$), 1.25 (3H, d, $CH_3$), 1.20-2.65 (6H, m, $CH+CH_2$) [fine structure was unresolved]; $^{13}$C NMR (THF-$d_8$): 14.0 ($CH_3$, br), 19.1 ($CH_3$, br), 36.4 (($CH_2$)$_2$, d), 41.8 (CH—P, br), 46.4 (CH—P, br); $^{31}$P NMR (THF-$d_8$): +143.4 ppm.

The invention claimed is:

1. Process for preparing compounds of the formula (I)

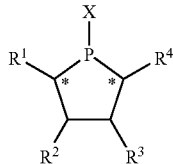

in which
* is a stereogenic center,
X is Cl, Br, or I,
$R^1$ and $R^4$ are each independently ($C_1$-$C_8$)-alkyl, ($C_1$-$C_8$)-alkoxy, HO—($C_1$-$C_8$)-alkyl, ($C_2$-$C_8$)-alkoxyalkyl, ($C_6$-$C_{18}$)-aryl, ($C_7$-$C_{19}$)-aralkyl, ($C_3$-$C_{18}$)-heteroaryl, ($C_4$-$C_{19}$)-heteroaralkyl, ($C_1$-$C_8$)-alkyl-($C_6$-$C_{18}$)-aryl, ($C_1$-$C_8$)-alkyl-($C_3$-$C_{18}$)-heteroaryl, ($C_3$-$C_8$)-cycloalkyl, ($C_1$-$C_8$)-alkyl-($C_3$-$C_8$)-cycloalkyl, or ($C_3$-$C_8$)-cycloalkyl-($C_1$-$C_8$)-alkyl,
$R^2$, $R^3$ are each independently $R^1$, OH or H, or
(a) $R^1$ and $R^2$ form a ($C_3$-$C_5$)-alkylene bridge together,
(b) $R^2$ and $R^3$ form a ($C_3$-$C_5$)-alkylene bridge together,
(c) $R^1$ and $R^3$ form a ($C_3$-$C_5$)-alkylene bridge together, or
(d) $R^2$ and $R^4$ form a ($C_3$-$C_5$)-alkylene bridge together, wherein
compounds of the formula (II)

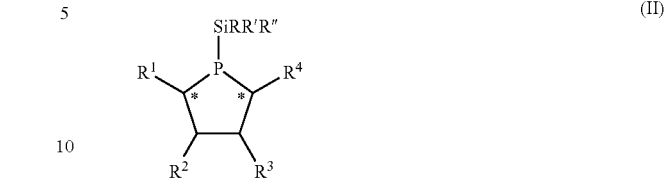

in which
*, $R^1$, $R^2$, $R^3$, $R^4$ are each as defined above,
R, R', R" may each independently be $R^1$,
are reacted with halogenated compounds selected from the group consisting of halocarbon compounds which lack double bonds in which the ratio of carbon atoms to halogen atoms is 1:≧2.5, $CCl_3CN$, $CCl_3COOEt$, $CCl_{(3-x)}H_xC(=O)Cl$, $C_2Cl_4Br_2$, $Cl_2$, $Br_2$, $I_2$.

2. Process according to claim 1, wherein halogenated compounds selected from the group consisting of $CCl_4$, $CHCl_3$, $C_2Cl_6$, $C_2HCl_5$, $C_2Cl_4Br_2$, $Cl_2$, $Br_2$, $I_2$ are used.

3. Process according to claim 1, wherein the reaction is carried out in an organic solvent selected from the group consisting of $CH_2Cl_2$ and $CHCl_3$.

4. Process according to claim 1, wherein the reaction is carried out at a temperature of 0-120° C.

5. Compounds of the formula (I)

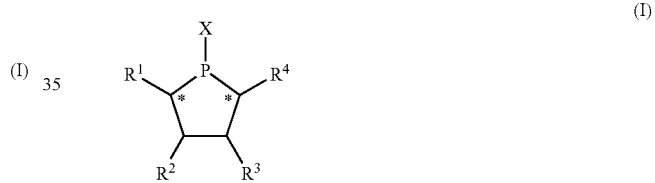

in which
* is a stereogenic center,
X is Cl, Br, or I,
$R^1$ and $R^4$ are each independently ($C_1$-$C_8$)-alkyl, ($C_1$-$C_8$)-alkoxy, HO—($C_1$-$C_8$)-alkyl, ($C_2$-$C_8$)-alkoxyalkyl, ($C_6$-$C_{18}$)-aryl, ($C_7$-$C_{19}$)-aralkyl, ($C_3$-$C_{18}$)-heteroaryl, ($C_4$-$C_{19}$)-heteroaralkyl, ($C_1$-$C_8$)-alkyl-($C_6$-$C_{18}$)-aryl, ($C_1$-$C_8$)-alkyl-($C_3$-$C_{18}$)-heteroaryl, ($C_3$-$C_8$)-cycloalkyl, ($C_1$-$C_8$)-alkyl-($C_3$-$C_8$)-cycloalkyl, or ($C_3$-$C_8$)-cycloalkyl-($C_1$-$C_8$)-alkyl,
$R^2$ and $R^3$ are each independently $R^1$, OH or H, or
(a) $R^1$ and $R^2$ form a ($C_3$-$C_5$)-alkylene bridge together,
(b) $R^2$ and $R^3$ form a ($C_3$-$C_5$)-alkylene bridge together,
(c) $R^1$ and $R^3$ form a ($C_3$-$C_5$)-alkylene bridge together, or
(d) $R^2$ and $R^4$ form a ($C_3$-$C_5$)-alkylene bridge together.

6. Process according to claim 1 wherein the reaction is carried out at a temperature of 20-80° C.

7. Process according to claim 1 wherein the reaction is carried out at a temperature of 30-50° C.

* * * * *